United States Patent [19]

Crump et al.

[11] Patent Number: 4,680,396

[45] Date of Patent: Jul. 14, 1987

[54] BIS(AMINOALKYL)PIPERAZINE DERIVATIVES AND THEIR USE AS METAL ION CONTROL AGENTS

[75] Inventors: Druce K. Crump, Lake Jackson; Jaime Simon, Angleton; David A. Wilson, Richwood, all of Tex.

[73] Assignee: The Dow Chemical Company, Midland, Mich.

[21] Appl. No.: 583,526

[22] Filed: Feb. 24, 1984

[51] Int. Cl.$^4$ .......................................... C07D 295/12
[52] U.S. Cl. .................... 544/337; 544/398; 544/399; 544/401
[58] Field of Search ............... 544/337, 398, 399, 401

[56] References Cited

U.S. PATENT DOCUMENTS

| | | | |
|---|---|---|---|
| 2,599,807 | 6/1952 | Bersworth | 260/502.5 R |
| 2,609,390 | 9/1952 | Bersworth | 260/502.5 R |
| 3,288,846 | 11/1966 | Trani et al. | 260/502.5 R |
| 3,331,773 | 7/1967 | Gunderson et al. | 210/698 |
| 3,336,221 | 8/1967 | Ralston | 210/700 |
| 3,401,151 | 9/1968 | Wieden et al. | 528/44 X |
| 3,434,969 | 3/1969 | Ralston | 210/700 |
| 3,674,804 | 7/1972 | Redmore | 544/337 J |
| 3,720,498 | 3/1973 | Redmore | 252/389 A |
| 3,743,603 | 7/1973 | Redmore | 252/180 |
| 3,859,211 | 1/1975 | Redmore | 210/729 |
| 3,954,761 | 5/1976 | Redmore | 544/337 |
| 4,051,110 | 9/1977 | Quinlan | 252/389 A |
| 4,500,356 | 2/1985 | Crump et al. | 544/337 X |
| 4,560,548 | 12/1985 | Simon et al. | 544/402 X |

OTHER PUBLICATIONS

Kobayashi et al., Chem. Abstracts, vol. 78, (1973).
Proc. Int. Water Conf., Eng. Soc. West PA., 41, pp. 167–174 (1980) "Toward a Better Understanding of Commercial Organophosphonates", Roderick A. Campbell.
Proc. Int. Water Conf., Eng. Soc., West PA., 39, pp. 89–99 (1978) "Scale and Deposit Control in Cooling Water Systems", Jeffrey R. Townsend, Karl W. Heiman.
Hoechst Organic Chemicals brochure title page and pp. 4, 14 and 15.

Primary Examiner—Donald G. Daus
Assistant Examiner—William A. Teoli, Jr.
Attorney, Agent, or Firm—A. C. Ancona

[57] ABSTRACT

It has now been found that certain phosphonate derivatives of bis(aminoalkyl) piperazines are good threshold agents to prevent metal ion precipitation in aqueous solutions. They also function as sequestering and/or chelating agents as do those which do not contain the phosphonate group.

21 Claims, No Drawings

BIS(AMINOALKYL)PIPERAZINE DERIVATIVES AND THEIR USE AS METAL ION CONTROL AGENTS

BACKGROUND OF THE INVENTION

The use of methylenephosphonic acid substituted alkylene polyamines for metal ion control at less than stoichiometric amounts was suggested in a patent to Bersworth (U.S. Pat. No. 2,609,390) in 1952. Later a water dispersible polymeric amine chelating agent which included alkylene phosphonate derivatives was indicated as having "threshold" effects in scale inhibition applications (U.S. Pat. No. 3,331,773), this term being used to describe the use of the agent in less than stoichiometric amounts. The diamine and polyamine methylenephosphonate derivatives are taught and claimed in U.S. Pat. Nos. 3,336,221 and 3,434,969, respectively. Some of the products disclosed in these two patents are available commercially and are recommended as scale inhibitors when applied in threshold amounts.

Some other patents which disclose heterocyclic nitrogen containing compounds which are useful as chelating agents and may be employed in threshold amounts are U.S. Pat. No. 3,674,804; 3,720;498; 3,743,603; 3,859,211; and 3,954,761. Some of the compounds included therein are heterocyclic compounds having the formulas:

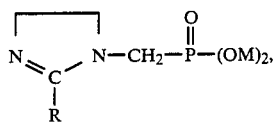

wherein R is hydrogen or alkyl and M is hydrogen, alkali metal, ammonium or a di- or triethanolamine radical;

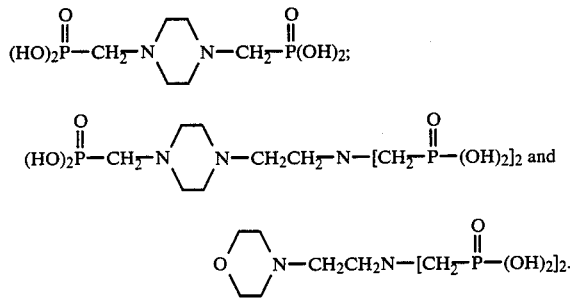

Methylenephosphonates of polyalkylene polyamines, disclosed in U.S. Pat. No. 4,051,110, are made by reacting di- or polyamines with a chain extending agent such as a dihalide or an epoxyhalide, e.g. ethylene dichloride or epichlorohydrin and thereafter, with phosphorous acid and formaldehyde. Thus, for example, triethylenetetramine is reacted with epichlorohydrin in an approximately one to one mole ratio; thereafter the product is reacted with phosphorous acid, and formaldehyde in the presence of hydrochloric acid. The resulting methylenephosphonated polyamine is useful in small amounts as a scale inhibitor, being employed at concentrations of 20–50 ppm.

Certain phosphonic acid derivatives of the aliphatic acids can be prepared by reacting phosphorous acid with acid anhydrides or acid chlorides, e.g. the anhydrides or chlorides of acetic, propionic and valeric acids. The compounds prepared have the formula

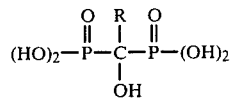

wherein R is a lower alkyl radical having 1 to 5 carbon atoms. The method of making and use of these products is described in U.S. Pat. No. 3,214,454. It discloses and claims the use of threshold amounts to prevent calcium precipitation in aqueous solutions.

SUMMARY OF THE INVENTION

It has now been found that certain phosphonate derivatives of bis(aminoalkyl)piperazines are good threshold agents to prevent metal ion precipitation in aqueous solutions. They also function as sequestering and/or chelating agents as do those which do not contain the phosphonate group.

DETAILED DESCRIPTION OF THE INVENTION

While the trimethylenephosphonate of aminoethylpiperazine itself has been shown not have very good threshold activity, the related derivatives of bis-(aminoalkyl)piperazine are quite effective.

The compounds from which the methylenephosphonates are derived have the formula

wherein n is 2 or 3.

These compounds can be made from piperazine and acrylonitrile or glycolonitrile, followed by reduction to the amine. The bis(aminopropyl) compound is commercially available.

The bis-amine is then reacted with phosphorus acid and formaldehyde (or a source of formaldehyde) as shown in Example 1 below. This phosphonomethylation is known to the art and is shown in a number of patents including U.S. Pat. Nos. 3,336,221 and 4,051,110.

The compounds produced by this phosphonomethylation which are the subject of the present invention have the formula

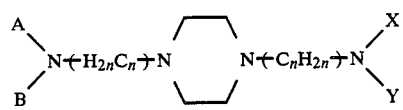

wherein n is 2 or 3 and wherein substituents A, B, X and Y each are independently selected from radicals consisting of hydrogen, hydroxyalkyl (wherein the alkyl group contains 2–6 carbon atoms), methylenephosphonic, methylene-, ethylene- and propylene-sulfonic, hydroxymethyl-, hydroxyethyl- and hydroxypropyl-sulfonic acid radicals, carboxylic acid radicals (having 2–4 carbon atoms) and the alkali or alkaline earth metal, ammonia and amine salts of any of the phosphonic, sulfonic or carboxylic acid derivatives. At least one of the substituents must be other than a hydrogen.

All the above substituents for the hydrogens of the amine groups of the above bis amine compounds form useful chelating agents, but only the methylenephosphonic acid substituted compounds and their alkali or alkaline earth metal, ammonium or amine salt derivatives are effective as threshold agents.

The following examples show the preparation of the subject compounds and their use as threshold and chelating agents.

EXAMPLE 1

Deionized water (10 g) and 20.0 g (0.10 mole) of bis(aminopropyl)piperazine were weighed into a 250-ml round-bottom reaction flask equipped with a water-cooled reflux condenser, mechanical stirrer, thermometer with a temperature controller, and an addition funnel. Approximately 40 g of concentrated HCl solution and 38.5 g (0.47 mole) of phosphorous acid were added to the aqueous amine solution and the reaction mixture heated to reflux and maintained for one hour. Aqueous 37% formaldehyde solution (34.0 g—0.42 mole) was added to the addition funnel and added over a one-hour period. The reaction mixture was heated at reflux for an additional four hours and then cooled. The product was the completely phosphonomethylated bis(aminopropyl)piperazine.

In like manner other experiments were conducted except that different amounts of reactants were used and some of the products were neutralized with caustic. Conditions are listed in Table I below.

TABLE I

| Example* | Bis amine | Amt. | HCl | $H_3PO_3$ | HCHO | NaOH |
|---|---|---|---|---|---|---|
| 2 | aminopropyl | 20 g | 40 g | 0.35 mole | 0.32 mole | — |
| 3 | aminoethyl | 17.2 g | 40 g | 0.47 mole | 0.42 mole | neut. |
| 4 | aminoethyl | 17.2 g | 40 g | 0.35 mole | 0.32 mole | neut. |

*The products are identified as follows: Example 2 contained three mole equivalents of methylenephosphonic acid functionality and one mole equivalent of hydrogen functionality. Example 3 contained four mole equivalents of methylenephosphonic acid functionality in the sodium form. Example 4 contained the same functionalities and ratios as in Example 2.

EXAMPLE 5

The procedure of Example 4 was repeated and the reaction product carboxymethylated using 0.12 mole of aqueous glycolonitrile ($HOCH_2C\equiv N$) in the presence of excess caustic to produce the sodium salt. The product contained an average of one mole equivalent of carboxymethyl functionality and three mole equivalents of methylenephosphonic acid functionality, all in the sodium form.

EXAMPLE 6

Deionized water (15.2 g) and 16.2 g (0.094 mole) of bis(aminoethyl)piperazine were weighed into a 250-ml round-bottom reaction flask equipped with a water-cooled reflux condenser, mechanical stirrer, thermometer with a temperature controller, and an addition funnel. Caustic solution (2.2 g of 50%) and 18.7 g (0.095 mole) of 3-chloro-2-hydroxy-1-propanesulfonic acid, sodium salt were added with stirring and the reaction mixture heated at 90° C. for two hours. Approximately 43 g of concentrated HCl solution and 33.1 g (0.28 mole) of 70% aqueous phosphorous acid solution were added and the reaction mixture heated to reflux and maintained for one hour. Aqueous 37% formaldehyde solution (22.9 g—0.28 mole) was added to the addition funnel and added over about a one-hour period. The reaction mixture was heated at reflux for an additional 2½ hours and then cooled. The final product solution was neutralized with potassium hydroxide solution. It contained an average of one mole equivalent of hydroxypropylsulfonate functionality and three mole equivalents of methylenephosphonate functionality.

EXAMPLE 7

The procedure of Example 6 was followed using 18.8 g (0.094 mole) of bis(aminopropyl)piperazine. The final product solution was not neutralized. It contained the same functional groups and ratios as Example 6 above, but derived from the bis(aminopropyl)piperazine, in the acid rather than salt form.

EXAMPLE 8

Propylene oxide (7 g—0.12 mole) was reacted with 16.2 g (0.094 mole) of bis(aminoethyl)piperazine and the reaction product then phosphonomethylated according to the procedure of Example 1 using 0.28 mole of phosphorous acid and formaldehyde solution. The final product solution was neutralized with KOH solution. It contained an average of one mole equivalent of hydroxypropyl functionality and three mole equivalents of methylenephosphonate functionality.

EXAMPLE 9

Bis(aminoethyl)piperazine was reacted with glycolonitrile in the presence of excess caustic to produce the tetrasodium salt of bis(aminoethyl)piperazinetetraacetic acid.

EXAMPLE A (Comparative)

Aminoethyl piperazine (AEP) was phosphonomethylated to obtain aminoethylpiperazine trimethylenephosphonic acid, the completely phosphonated AEP.

To show the utility of the above compounds as scale inhibitors, the following test was run.

Calcium Scale Inhibitor Test

The compounds were evaluated as scale inhibitors for calcium carbonate scale according to National Association of Corrosion Engineers (NACE) test method TM-03-74. The results are shown in Table II. Note the dramatic improvement of the phosphonic acids prepared from the bis(aminoethyl)piperazine and bis(aminopropyl)piperazine compounds of this invention when compared to aminoethylpiperazinetrimethylenephosphonic acid taught in the U.S. patent literature as a good scale inhibition compound.

TABLE II

| | Scale Inhibition Data | | | |
|---|---|---|---|---|
| | Concentration* | Percent Inhibition at | | |
| Compound | (ppm) | 24 Hrs. | 48 Hrs. | 72 Hrs. |
| Example A (comparative) | 10 | 77 | 65 | 60 |
| Example 1 | 10 | 99 | 93 | 90 |
| Example 2 | 10 | 99 | 93 | 91 |
| Example 3 | 10 | 99 | 91 | 89 |
| Example 4 | 10 | 97 | 87 | 79 |
| Example 5 | 10 | 96 | 89 | 83 |
| Example 6 | 10 | 85 | 73 | 75 |

TABLE II-continued

| Compound | Concentration* (ppm) | Percent Inhibition at | | |
|---|---|---|---|---|
| | | 24 Hrs. | 48 Hrs. | 72 Hrs. |
| Example 7 | 10 | 92 | 77 | 79 |
| Example 8 | 10 | 79 | 77 | 73 |
| Example 9** | 10 | 55 | 51 | 50 |
| Blank (none) | — | 52 | 51 | 50 |

*ppm based on active acid content
**this is not a good threshold compound, but see below for utility as chelating or sequestering agent The compounds of this invention can also function as sequestering/chelating agents. For example, compounds were titrated with standard copper solution in the presence of chrome azurol-S indicator. The compound of Example 9 complexed about one mole of copper per mole of ligand. Thus the compound of Example 9, although ineffective as a threshold compound, can be utilized as a chelating agent. The compound of Example 3 was titrated and found to complex approximately three moles of copper per mole of ligand. The compound can function as either a threshold compound or a chelating agent.

The compounds of the invention which contain one or more methylenephosphonic acid radicals as substituents on the primary amine nitrogens can be used as threshold agents to prevent the precipitation of metal ions, e.g. $Ca^{++}$, $Mg^{++}$, $Ba^{++}$, and the like. They are employed at substoichiometric amounts based on the metal ions present, the precipitation of which is to be prevented.

These and the remaining compounds which do not contain the methylene phosphonate radical may be employed as chelating agents when used at or near stoichiometric quantities.

We claim:

1. The compounds having the formula

wherein n is 2 or 3 and wherein substituents A, B, X and Y each are independently selected from the group consisting of hydrogen, hydroxyalkyl (wherein the alkyl group has 2-6 carbon atoms), methylenephosphonic, hydroxymethyl-, hydroxyethyl- and hydroxypropylsulfonic acid radicals, carboxylic acid radicals (having 2-4 carbon atoms) and the alkali, alkaline earth metal, ammonium and amine salts of any of the phosphonic, sulfonic or carboxylic acid compounds, and wherein at least one of A, B, X and Y is other than a hydrogen.

2. The compounds of claim 1 wherein n is 2.
3. The compounds of claim 1 wherein n is 3.
4. The compounds of claim 2 wherein each of A, B, X and Y are —$CH_2$—$PO_3R_2$ and R is a hydrogen atom or an alkali or an alkaline earth metal atom.
5. The compounds of claim 3 wherein each of A, B, X and Y are —$CH_2$—$PO_3R_2$ and R is a hydrogen atom or an alkali or an alkaline earth metal atom.
6. The compound of claim 2 wherein three of A, B, X and Y substituents are $CH_2PO_3H_2$ and the remaining one is hydrogen.
7. The compound of claim 3 wherein three of A, B, X and Y substituents are $CH_2PO_3H_2$ and the remaining one is hydrogen.
8. The compound of claim 6 wherein the phosphonic acid substituents are in the salt form.
9. The compound of claim 7 wherein the phosphonic acid substituents are in the salt form.
10. The compound of claim 8 wherein the salt is a sodium salt.
11. The compound of claim 9 wherein the salt is a sodium salt.
12. The compound of claim 2 wherein three of A, B, X and Y substituents are $CH_2PO_3H_2$ and the remaining one is $CH_2COOH$.
13. The compound of claim 12 wherein all the acid groups are in the salt form.
14. The compound of claim 13 wherein the salt is a sodium salt.
15. The compound of claim 3 wherein three of A, B, X and Y substituents are $CH_2PO_3H_2$ and the remaining one is $CH_2COOH$.
16. The compound of claim 15 wherein all the acid groups are in the salt form.
17. The compound of claim 16 wherein the salt is a sodium salt.
18. The compounds of claim 2 wherein three of A, B, X and Y substituents are $CH_2PO_3R_2$ and the remaining one is $CH_2CH(OH)CH_2SO_3R$ wherein R is hydrogen, an alkali or alkaline earth metal.
19. The compound of claim 18 wherein R is sodium.
20. The compound of claim 3 wherein three of A, B, X and Y substituents are $CH_2PO_3R_2$ and the remaining one is $CH_2CH(OH)CH_2SO_3R$ wherein R is hydrogen, an alkali or alkaline earth metal.
21. The compound of claim 20 wherein R is sodium.

* * * * *